United States Patent [19]
Dassel et al.

[11] Patent Number: 6,156,868
[45] Date of Patent: *Dec. 5, 2000

[54] METHODS FOR PREPARING POLYMERS FROM DIBASIC ACIDS

[75] Inventors: Mark William Dassel, Indianola; David Cole DeCoster, Buckley; Ader Meherban Rostami, Bainbridge Island; Sharon Marie Aldrich, Poulsbo, all of Wash.; Eustathios Vassiliou, Newark, Del.

[73] Assignee: RPC Inc., Atlanta, Ga.

[*] Notice: This patent is subject to a terminal disclaimer.

[21] Appl. No.: 09/311,618

[22] Filed: May 13, 1999

Related U.S. Application Data

[63] Continuation of application No. 08/824,992, Mar. 27, 1997.
[60] Provisional application No. 60/020,798, Jun. 24, 1996, abandoned.

[51] Int. Cl.⁷ .............................. C08G 73/00; C08G 63/02
[52] U.S. Cl. .......................... 528/310; 528/170; 528/172; 528/183; 528/179; 528/272; 528/274; 528/308; 528/308.6; 528/332; 528/335; 528/336; 528/345
[58] Field of Search ...................... 528/310, 272, 528/308, 308.6, 335, 170, 172, 179, 183, 274, 332, 336, 345

[56] References Cited

U.S. PATENT DOCUMENTS

| | | | |
|---|---|---|---|
| 1,121,532 | 12/1914 | Newberry | 23/299 |
| 2,014,044 | 9/1935 | Haswell | 75/17 |
| 2,223,493 | 12/1940 | Loder et al. | 260/537 |
| 2,223,494 | 12/1940 | Loder et al. | 260/586 |
| 2,301,240 | 11/1942 | Baumann et al. | 183/115 |
| 2,439,513 | 4/1948 | Hamblet et al. | 260/533 |
| 2,557,282 | 6/1951 | Hamblet et al. | 260/533 |
| 2,565,087 | 8/1951 | Porter et al. | 260/631 |
| 2,980,523 | 4/1961 | Dille et al. | 48/215 |
| 3,161,603 | 12/1964 | Leyshon et al. | 252/413 |
| 3,231,608 | 1/1966 | Kollar | 260/533 |
| 3,234,271 | 2/1966 | Barker et al. | 260/531 |
| 3,290,369 | 12/1966 | Bonfield et al. | 260/537 |
| 3,361,806 | 1/1968 | Lidov et al. | 260/531 |
| 3,515,751 | 6/1970 | Oberster et al. | 260/533 |
| 3,530,185 | 9/1970 | Pugi | 260/586 |
| 3,613,333 | 10/1971 | Gardenier | 55/89 |
| 3,677,696 | 7/1972 | Bryk et al. | 23/2 |
| 3,928,005 | 12/1975 | Laslo | 55/73 |
| 3,932,513 | 1/1976 | Russell | 260/586 |
| 3,946,076 | 3/1976 | Paasen et al. | 260/586 |
| 3,957,876 | 5/1976 | Rapoport et al. | 260/586 |
| 3,987,100 | 10/1976 | Bernette et al. | 260/586 |
| 3,987,808 | 10/1976 | Carbonell et al. | 137/3 |
| 4,039,304 | 8/1977 | Bechthold et al. | 55/10 |
| 4,055,600 | 10/1977 | Langley et al. | 260/586 |
| 4,065,527 | 12/1977 | Graber | 261/79 A |
| 4,308,037 | 12/1981 | Meissner et al. | 55/10 |
| 4,361,965 | 12/1982 | Goumondy et al. | 34/57 |
| 4,370,304 | 1/1983 | Hendriks et al. | 422/224 |
| 4,394,139 | 7/1983 | Board | 55/20 |
| 4,419,184 | 12/1983 | Backlund | 162/49 |
| 4,423,018 | 12/1983 | Lester, Jr. et al. | 423/243 |
| 5,061,453 | 10/1991 | Krippl et al. | 422/106 |
| 5,104,492 | 4/1992 | King et al. | 203/15 |
| 5,123,936 | 6/1992 | Stone et al. | 55/8 |
| 5,170,727 | 12/1992 | Nielsen | 110/346 |
| 5,221,800 | 6/1993 | Park et al. | 562/543 |
| 5,244,603 | 9/1993 | Davis | 261/87 |
| 5,270,019 | 12/1993 | Melton et al. | 422/234 |
| 5,271,904 | 12/1993 | Esposito et al. | 422/105 |
| 5,286,458 | 2/1994 | Yang et al. | 422/168 |
| 5,294,378 | 3/1994 | Succi et al. | 261/130 |
| 5,312,567 | 5/1994 | Kozma et al. | 261/87 |
| 5,321,157 | 6/1994 | Kollar | 562/543 |
| 5,374,767 | 12/1994 | Drinkard et al. | 560/193 |
| 5,396,850 | 3/1995 | Conochie et al. | 110/346 |
| 5,399,750 | 3/1995 | Brun et al. | 562/553 |
| 5,463,119 | 10/1995 | Kollar | 562/543 |
| 5,502,245 | 3/1996 | Dassel et al. | 562/413 |

(List continued on next page.)

FOREIGN PATENT DOCUMENTS

| | | |
|---|---|---|
| 439 007 A2 | 7/1991 | European Pat. Off. |
| 751 105 A2 | 1/1997 | European Pat. Off. |
| 2 722 783 A1 | 1/1996 | France. |
| 1143213 | 2/1969 | Germany. |
| 4426132A1 | 1/1996 | Germany. |
| 415172 | 8/1934 | United Kingdom. |
| 738808 | 10/1955 | United Kingdom. |
| WO 96/03365 | 2/1996 | WIPO. |
| WO96/03365 | 2/1996 | WIPO. |
| WO 96/40610 | 12/1996 | WIPO. |

OTHER PUBLICATIONS

E. Sorribes et al., "Formación de neuvas fases en el proceso de obtención de ácido adípico: causas y efectos que provocan," *Rev. R. Acad. Cienc. Exactas, Fis. Nat. Madrid* (1987), 81 (1), 233–5 (+English language translation).

*Primary Examiner*—P. Hampton-Hightower
*Attorney, Agent, or Firm*—Seed Intellectual Property Law Group PLLC

[57] ABSTRACT

This invention relates to methods of preparing dibasic acids, such as adipic acid for example, by oxidizing a hydrocarbon with a gas containing an oxidant, preferably oxygen. A respective hydrocarbon is reacted with a gaseous oxidant to form dibasic acid in a mixture which preferably contains a solvent, a catalyst, and an initiator. The temperature of the mixture is then lowered to a point at which solid dibasic acid is precipitated, while maintaining a single liquid phase. At least part of the formed acid is then removed. The lowering of the temperature is preferably performed at least partially by an operation selected from a group consisting of (a) evaporating at least part of the hydrocarbon or otherwise adjusting the hydrocarbon content of the mixture (b) lowering the pressure (c) adding matter having a temperature lower than the initial temperature (d) removing heat by external means (e) removing a first amount of heat by any suitable means, and adding a second amount of heat by external means, the first amount of heat being greater than the second amount of heat, and (f) a combination thereof.

32 Claims, 3 Drawing Sheets

U.S. PATENT DOCUMENTS

| | | | |
|---|---|---|---|
| 5,558,842 | 9/1996 | Vassiliou et al. | 422/108 |
| 5,580,531 | 12/1996 | Vassiliou et al. | 422/108 |
| 5,654,475 | 8/1997 | Vassiliou et al. | 562/413 |
| 5,801,273 | 9/1998 | Vassiliou et al. | 562/413 |
| 5,801,282 | 9/1998 | Dassel et al. | 562/413 |
| 5,817,868 | 10/1998 | Rostami et al. | 562/413 |
| 5,824,819 | 10/1998 | Dassel et al. | 562/529 |
| 5,877,341 | 3/1999 | Vassiliou et al. | 560/77 |
| 5,883,292 | 3/1999 | Dassel et al. | 562/413 |
| 5,922,908 | 7/1999 | Dassel et al. | 562/543 |
| 5,939,582 | 8/1999 | Dassel et al. | 562/413 |
| 5,980,801 | 11/1999 | Dassel et al. | 264/176.1 |
| 5,998,572 | 12/1999 | Rostami et al. | 528/322 |

METHODS FOR PREPARING POLYMERS FROM DIBASIC ACIDS

CROSS-REFERENCE TO RELATED APPLICATIONS

The present application is a continuation of U.S. application Ser. No. 08/824,992, filed Mar. 27, 1997 (now allowed); which claims priority to U.S. Provisional Application Ser. No. 60/020,798, filed Jun. 24, 1996, abandoned which applications are incorporated herein by reference in their entirety.

FIELD OF THE INVENTION

This invention relates to methods of preparing dibasic acids, such as adipic acid for example, by oxidizing a hydrocarbon with a gas containing an oxidant, preferably oxygen.

BACKGROUND OF THE INVENTION

There is a plethora of references (both patents and literature articles) dealing with the formation of diacids, one of the most important being adipic acid. Adipic acid is used to produce Nylon 66 fibers and resins, polyesters, polyurethanes, and miscellaneous other compounds.

There are different processes of manufacturing adipic acid. The conventional process involves a first step of oxidizing cyclohexane with oxygen to a mixture of cyclohexanone and cyclohexanol (KA mixture), and then oxidation of the KA mixture with nitric acid to adipic acid. Other processes include, among others, the "Hydroperoxide Process", the "Boric Acid Process", and the "Direct Synthesis Process", which involves direct oxidation of cyclohexane to adipic acid with oxygen in the presence of solvents, catalysts, and promoters.

The Direct Synthesis Process has been given attention for a long time. However, to this date it has found little commercial success. One of the reasons is that although it looks very simple at first glance, it is extremely complex in reality. Due to this complexity, one can find strikingly conflicting results, comments, and views in different references.

It is well known that after a reaction has taken place according to the Direct Synthesis, a mixture of two liquid phases is present at ambient temperature, along with a solid phase mainly consisting of adipic acid. The two liquid phases have been called the "Polar Phase" and the "Non-Polar Phase". However, no attention has been paid so far to the importance of the two phases, except for separating the adipic acid from the "Polar Phase" and recycling these phases to the reactor partially or totally with or without further treatment.

It is also important to note that most, if not all, studies on the Direct Oxidation have been conducted in a batch mode, literally or for all practical purposes.

There is a plethora of references dealing with oxidation of organic compounds to produce acids, such as, for example, adipic acid and/or intermediate products, such as for example cyclohexanone, cyclohexanol, cyclohexylhydroperoxide, etc.

The following references, among the plethora of others, may be considered as representative of oxidation processes relative to the preparation of diacids and intermediate products.

U.S. Pat. No. 5,463,119 (Kollar) discloses a process for the oxidative preparation of $C_5$–$C_8$ aliphatic dibasic acids by (1) reacting,
  (a) at least one saturated cycloaliphatic hydrocarbon having from 5 to 8 ring carbon atoms in the liquid phase and
  (b) an excess of oxygen gas or an oxygen-containing gas in the presence of
  (c) a solvent comprising an organic acid containing only primary and/or secondary hydrogen atoms and
  (d) at least about 0.002 mole per 1000 grams of reaction mixture of a polyvalent heavy metal catalyst;
(2) removing the aliphatic dibasic acid; and
(3) recycling intermediates, post oxidation components, and derivatives thereof remaining after removal of the aliphatic dibasic acid into the oxidation reaction.

U.S. Pat. No. 5,374,767 (Drinkard et al) discloses formation of cyclohexyladipates in a staged reactor, e.g. a reactive distillation column. A mixture containing a major amount of benzene and a minor amount of cyclohexene is fed to the lower portion of the reaction zone and adipic acid is fed to the upper portion of the reaction zone, cyclohexyladipates are formed and removed from the lower portion of the reaction zone and benzene is removed from the upper portion of the reaction zone. The reaction zone also contains an acid catalyst.

U.S. Pat. No. 5,321,157 (Kollar) discloses a process for the preparation of $C_5$–$C_8$ aliphatic dibasic acids through oxidation of corresponding saturated cycloaliphatic hydrocarbons by (1) reacting, at a cycloaliphatic hydrocarbon conversion level of between about 7% and about 30%,
  (a) at least one saturated cycloaliphatic hydrocarbon having from 5 to 8 ring carbon atoms in the liquid phase and
  (b) an excess of oxygen gas or an oxygen containing gas mixture in the presence of
  (c) less than 1.5 moles of a solvent per mole of cycloaliphatic hydrocarbon (a), wherein said solvent comprises an organic acid containing only primary and/or secondary hydrogen atoms and
  (d) at least about 0.002 mole per 1000 grams of reaction mixture of a polyvalent heavy metal catalyst; and
(2) isolating the C5–C8 aliphatic dibasic acid.

U.S. Pat. No. 5,221,800 (Park et al) discloses a process for the manufacture of adipic acid. In this process, cyclohexane is oxidized in an aliphatic monobasic acid solvent in the presence of a soluble cobalt salt wherein water is continuously or intermittently added to the reaction system after the initiation of oxidation of cyclohexane as indicated by a suitable means of detection, and wherein the reaction is conducted at a temperature of about 50° C. to about 150° C. at an oxygen partial pressure of about 50 to 420 pounds per square inch absolute.

U.S. Pat. No. 3,987,100 (Bamete et al.) describes a process of oxidizing cyclohexane to produce cyclohexanone and cyclohexanol, said process comprising contacting a stream of liquid cyclohexane with oxygen in each of at least three successive oxidation stages by introducing into each stage a mixture of gases comprising molecular oxygen and an inert gas.

U.S. Pat. No. 3,957,876 (Rapoport et al.) describes a process for the preparation of cyclohexyl hydroperoxide substantially free of other peroxides by oxidation of cyclohexane containing a cyclohexane soluble cobalt salt in a zoned oxidation process in which an oxygen containing gas is fed to each zone in the oxidation section in an amount in excess of that which will react under the conditions of that zone.

U.S. Pat. No. 3,932,513 (Russell) discloses the oxidation of cyclohexane with molecular oxygen in a series of reaction zones, with vaporization of cyclohexane from the last reactor effluent and parallel distribution of this cyclohexane vapor among the series of reaction zones.

U.S. Pat. No. 3,530,185 (Pugi) discloses a process for manufacturing precursors of adipic acid by oxidation with an oxygen-containing inert gas which process is conducted in at least three successive oxidation stages by passing a stream of liquid cyclohexane maintained at a temperature in the range of 140° to 200° C. and a pressure in the range of 50 to 350 p.s.i.g. through each successive oxidation stage and by introducing a mixture of gases containing oxygen in each oxidation stage in an amount such that substantially all of the oxygen introduced into each stage is consumed in that stage thereafter causing the residual inert gases to pass countercurrent into the stream of liquid during the passage of the stream through said stages.

U.S. Pat. No. 3,515,751 (Oberster et al) discloses a process for the production of epsilon-hydroxycaproic acid in which cyclohexane is oxidized by liquid phase air oxidation in the presence of a catalytic amount of a lower aliphatic carboxylic acid and a catalytic amount of a peroxide under certain reaction conditions so that most of the oxidation products are found in a second, heavy liquid layer, and are directed to the production of epsilon-hydroxycaproic acid.

U.S. Pat. No. 3,361,806 (Lidov et al) discloses a process for the production of adipic acid by the further oxidation of the products of oxidation of cyclohexane after separation of cyclohexane from the oxidation mixture, and more particularly to stage wise oxidation of the cyclohexane to give high yields of adipic acid precursors and also to provide a low enough concentration of oxygen in the vent gas so that the latter is not a combustible mixture.

U.S. Pat. No. 3,234,271 (Barker et al) discloses a process for the production of adipic acid by the two-step oxidation of cyclohexane with oxygen. In a preferred embodiment, mixtures comprising cyclohexanone and cyclohexanol are oxidized. In another embodiment, the process involves the production of adipic acid from cyclohexane by oxidation thereof, separation of cyclohexane from the oxidation mixture and recycle thereof, and further oxidation of the other products of oxidation.

U.S. Pat. No. 3,231,608 (Kollar) discloses a process for the preparation of aliphatic dibasic acids from saturated cyclic hydrocarbons having from 4 to 8 cyclic carbon atoms per molecule in the presence of a solvent which comprises an aliphatic monobasic acid which contains only primary and secondary hydrogen atoms and a catalyst comprising a cobalt salt of an organic acid, and in which process the molar ratio of said solvent to said saturated cyclic hydrocarbon is between 1.5:1 and 7:1, and in which process the molar ratio of said catalyst to to said saturated cyclic hydrocarbon is at least 5 millimoles per mole.

U.S. Pat. No. 3,161,603 (Leyshon et al) discloses a process for recovering the copper-vanadium catalyst from the waste liquors obtained in the manufacture of adipic acid by the nitric acid oxidation of cyclohexanol and/or cyclohexanone.

U.S. Pat. No. 2,565,087 (Porter et al) discloses the oxidation of cycloaliphatic hydrocarbons in the liquid phase with a gas containing molecular oxygen and in the presence of about 10% water to produce two phases and avoid formation of esters.

U.S. Pat. No. 2,557,282 (Hamblet et al) discloses production of adipic acid and related aliphatic dibasic acids; more particularly to the production of adipic acid by the direct oxidation of cyclohexane.

U.S. Pat. No. 2,439,513 (Hamblet et al) discloses the production of adipic acid and related aliphatic dibasic acids and more particularly to the production of adipic acid by the oxidation of cyclohexane.

U.S. Pat. No. 2,223,494 (Loder et al) discloses the oxidation of cyclic saturated hydrocarbons and more particularly to the production of cyclic alcohols and cyclic ketones by oxidation of cyclic saturated hydrocarbons with an oxygen-containing gas.

U.S. Pat. No. 2,223,493 (Loder et al) discloses the production of aliphatic dibasic acids and more particularly to the production of aliphatic dibasic acids by oxidation of cyclic saturated hydrocarbons with an oxygen-containing gas.

None of the above references, or any other references known to the inventors disclose, suggest or imply, singly or in combination, oxidation reactions to intermediate oxidation products under phase-controlled conditions subject to the intricate and critical controls and requirements of the instant invention as described and claimed.

Our U.S. Pat. Nos. 5,580,531, 5,558,842, 5,502,245, and our co-pending pending application Ser. No. 08/477,195 (filed Jun. 7, 1995, now U.S. Pat. No. 5,801,282), Ser. No. 08/587,967 (filed Jan. 17, 1996, now U.S. Pat. No. 5,883,292), and Ser. No. 08/620,974 (filed Mar. 25, 1996, now U.S. Pat. No. 5,654,475), all of which are incorporated herein by reference, describe methods and apparatuses relative to controlling reactions in atomized liquids. Our co-pending application, U.S. patent application Ser. No. 08/812,847, of Mark W. Dassel, Eustathios Vassiliou, David C. DeCoster, Ader M. Rostami, and Sharon M. Aldrich, titled "Methods and Devices for Controlling the Reaction Rate of a Hydrocarbon to an Acid by Making Phase-related Adjustments", filed on Mar. 6, 1997, is also incorporated herein by reference.

SUMMARY OF THE INVENTION

As aforementioned, this invention relates to methods and devices of making acids, such as adipic acid for example, by oxidizing a hydrocarbon with a gas containing an oxidant, preferably oxygen. Particularly, it pertains a method of preparing a dibasic acid in a reaction zone from a respective hydrocarbon in a mixture with a solvent and a catalyst at a first temperature and at a first pressure, the hydrocarbon being at a desired content of the mixture, the method comprising the steps of:

(a) reacting at least part of the hydrocarbon in the mixture being at the first temperature and at the first pressure with a gaseous oxidant to form at least part of the dibasic acid;

(b) lowering the first temperature to a second temperature, while maintaining one-liquid-phase at the second temperature; and (d) removing at least part of the formed acid;

The method of the instant invention may comprise a step of recycling at least part of one or more of products, by-products, reactants, solvents, off-gases, and other existing ingredients either directly to the reaction zone or indirectly after post-treatment, or a combination thereof.

The formation and maintenance of a single liquid phase may be controlled by adjusting the content of hydrocarbon, or water, or solvent, or a combination thereof, at the second temperature.

The lowering of the first temperature to the second temperature is preferably performed at least partially by an operation selected from a group consisting of (a) evaporating at least part of the hydrocarbon or otherwise adjusting the hydrocarbon content of the mixture (b) lowering the first pressure to a second pressure (c) adding matter having a temperature lower than the first temperature (d) removing heat by external means (e) removing a first amount of heat by any suitable means, and adding a second amount of heat by external means, the first amount of heat being greater than the second amount of heat, and (f) a combination thereof.

External means of either heating or cooling are means different than evaporation or addition of liquid having a different temperature than the material to be heated or cooled. The word "external" does not refer to a chamber and it does not mean "outside of a chamber". It includes, for example, heating or cooling coils, preferably inside a chamber.

The lowering of the first temperature to the second temperature may involve an intermediate step of lowering the first temperature to a first intermediate temperature by lowering the first pressure to an intermediate pressure to form a first intermediate, preferably single, phase liquid containing no substantial amount of solid phase.

The method may further comprise a step of providing heat to the first intermediate, preferably single, phase liquid for removing part of the hydrocarbon, and it may further comprise a step of lowering the temperature of the first intermediate, preferably single, phase liquid to the second temperature by lowering the intermediate pressure to the second pressure, and forming a final single phase liquid containing precipitated dibasic acid.

The method may further comprise a step of applying vacuum for attaining the second pressure. It may also comprise a step of removing heat with external means from the first intermediate, preferably single, phase liquid before it assumes the form of the final single phase liquid. Preferably, the step of removing heat with external means does not cause precipitation of a solid phase.

The methods of the instant invention are particularly suited in the case where the hydrocarbon comprises cyclohexane, the gaseous oxidant comprises oxygen, the dibasic acid comprises adipic acid, the solvent comprises acetic acid, and the catalyst comprises a multivalent heavy metal ion.

Further, the instant invention pertains to a method, wherein the dibasic acid comprises adipic acid, and the method further comprises a step of reacting the adipic acid with a third reactant selected from a group consisting of a polyol, a polyamine, and a polyamide in a manner to form a polymer of a polyester, or a polyamide, or a (polyimide and/or polyamideimide), respectively.

The method may further comprise a step of spinning the polymer into fibers.

Accordingly, the present invention provides a method of preparing a polymer from a dibasic acid, wherein the dibasic acid is prepared in a reaction zone from a respective hydrocarbon in a mixture with a solvent, a catalyst and water at a first temperature and at a first pressure, the hydrocarbon being at a desired hydrocarbon content, the solvent being at a desired solvent content, and the water being at a desired water content, the method comprising the steps of:

(a) reacting at least part of the hydrocarbon in the mixture being at the first temperature and at the first pressure with a gaseous oxidant to form at least part of the dibasic acid at a predetermined conversion range, lower than substantially complete conversion;

(b) lowering the first temperature to a second temperature with simultaneous at least partial precipitation of the dibasic acid, and with simultaneous removal of an effective amount of hydrocarbon to maintain a single liquid phase at the second temperature;

(c) removing at least part of the precipitated dibasic acid; and (d) reacting the dibasic acid with a reactant selected from a group consisting of a polyol, a polyamine, and a polyamide in a manner to form the polymer of a polyester, or a polyamide, or a (polyimide and/or polyamideimide), respectively.

In a related aspect, the invention provides a method of preparing a polymer from a dibasic acid, wherein the dibasic acid is prepared in a reaction zone from a respective hydrocarbon in a mixture with a solvent, a catalyst and water at a first temperature and at a first pressure, the hydrocarbon being at a desired hydrocarbon content, the solvent being at a desired solvent content, and the water being at a desired water content, the method comprising the steps of:

(a) reacting at least part of the hydrocarbon in the mixture being at the first temperature and at the first pressure with a gaseous oxidant to form at least part of the dibasic acid at a predetermined conversion range, lower than substantially complete conversion;

(b) lowering the first temperature to a second temperature, while maintaining a single liquid phase at the second temperature, wherein the lowering of the first temperature to the second temperature involves an intermediate step of lowering the first temperature to a first intermediate temperature by lowering the first pressure to an intermediate pressure to form a first intermediate liquid phase containing no substantial amount of solid phase, and wherein lowering of the intermediate temperature to the second temperature is conducted with simultaneous at least partial precipitation of the dibasic acid, and with simultaneous removal of an effective amount of hydrocarbon to maintain a single liquid phase at the second temperature;

(c) removing at least part of the precipitated dibasic acid; and (d) reacting the dibasic acid with a reactant selected from a group consisting of a polyol, a polyamine, and a polyamide in a manner to form the polymer of a polyester, or a polyamide, or a (polyimide and/or polyamideimide), respectively.

The instant invention also relates to a device for preparing a dibasic acid from a respective hydrocarbon in a mixture with a solvent and a catalyst at a first temperature and at a first pressure, the hydrocarbon being at a desired content of the mixture, the device comprising:

a first reaction chamber;

first temperature control means connected to the first reaction chamber for controlling the temperature in said first reaction chamber;

first pressure control means connected to the reaction chamber for controlling the pressure in said first reaction chamber;

first hydrocarbon feeding means connected to the first reaction chamber for feeding hydrocarbon into said first reaction chamber;

first gaseous oxidant feeding means connected to the first reaction chamber for feeding gaseous oxidant into said first reaction chamber;

a second chamber connected to the first reaction chamber;

second temperature control means connected to the second chamber for controlling the temperature in said second chamber;

second pressure control means connected to the second chamber for controlling the pressure in said second chamber;

second phase control means for maintaining the mixture in the second chamber in a single liquid phase; and separating means connected to or being part of the second chamber for separating at least partially the dibasic acid from the mixture.

The first reaction chamber and the second chamber may constitute one and the same reaction chamber.

The first reaction chamber may be connected to a first condenser, which in turn is preferably connected to a first retaining chamber. The first retaining chamber may also play the role of a decanter, for separating, for example, water of reaction and/or solvent from mainly hydrocarbon, for example.

The device may further comprise a second condenser connected to the second chamber, and a second retaining chamber may be also connected to the second condenser. Second hydrocarbon feeding means may be connected to the second chamber for feeding hydrocarbon into the second chamber. External cooling or heating means may be connected to the second chamber for cooling or heating the mixture, respectively, in the second chamber. A vacuum generator may preferably be also connected to the second retaining chamber.

The present invention also pertains a device for preparing a dibasic acid from a respective hydrocarbon in a mixture with a solvent and a catalyst at a first temperature and at a first pressure, the hydrocarbon being at a desired content of the mixture, the device comprising:

a first reaction chamber;

first temperature control means connected to the first reaction chamber for controlling the temperature in said first reaction chamber;

first pressure control means connected to the reaction chamber for controlling the pressure in said first reaction chamber;

first hydrocarbon feeding means connected to the first reaction chamber for feeding hydrocarbon into said first reaction chamber;

first gaseous oxidant feeding means connected to the first reaction chamber for feeding gaseous oxidant into said first reaction chamber;

a first intermediate chamber communicating with the first reaction chamber;

first intermediate temperature control means connected to the first intermediate chamber for controlling the temperature in said first intermediate chamber;

first intermediate pressure control means connected to the intermediate chamber for controlling the pressure in said first intermediate chamber;

first intermediate external heating means for providing thermal energy to matter inside the first intermediate chamber;

an intermediate condenser connected to the first intermediate chamber;

a second chamber connected to the first intermediate chamber;

second temperature control means connected to the second chamber for controlling the temperature in said second chamber;

second pressure control means connected to the second chamber for controlling the pressure in said second chamber;

a controller for controlling miscellaneous parameters in the chambers in a manner that in the second chamber there is a single liquid phase.

separating means connected to or being part of the second chamber for separating at least partially the dibasic acid from the mixture.

The device may further comprise:

a second intermediate chamber between the first intermediate chamber and the second chamber;

second intermediate external cooling means for removing thermal energy from matter inside the first intermediate chamber;

At least two of the chambers may constitute one and the same device.

BRIEF DESCRIPTION OF THE DRAWING

The reader's understanding of this invention will be enhanced by reference to the following detailed description taken in combination with the drawing figure, wherein.

DETAILED DESCRIPTION OF THE INVENTION

As aforementioned, this invention relates to methods of making acids, such as adipic acid for example, by oxidizing a hydrocarbon with a gas containing an oxidant, preferably oxygen.

According to the prior art, after a reaction has taken place in the Direct Synthesis of cyclohexane to adipic acid, a mixture of two liquid phases are present at ambient or lower temperatures, along with a solid phase mainly consisting of adipic acid. The two liquid phases have been called the "Polar Phase" and the "Non-Polar Phase". The two phases are decanted, and the adipic acid is further crystallized and separated from the "Polar Phase".

The presence of two liquid phases mixed with a solid phase and the precipitating acid from the "Polar Phase" along with the required filtration of the solid phase cause a very undesirable situation. Decanting itself is an undesirable additional step in a process, even if it is performed in the absence of a solid phase. The simultaneous presence of a solid phase, especially if part of the solid is dissolved in one of the liquid phases, and apt to precipitate upon any lowering of the temperature, or with time, brings about serious complications.

The inventors of the instant invention, have discovered that they can avoid the formation of a two-phase liquid system, and maintain a single liquid phase containing the solid phase, even at ambient or lower temperature using the techniques and devices described in detail hereinbelow. The absence of a second liquid phase, not only eliminates a decanting step, but also simplifies the whole process of separating the solid phase from the single liquid phase.

In addition to the formation of adipic acid, the methods of the present invention may also be applied to other dibasic acids from the corresponding cyclic aliphatic hydrocarbons. Examples are formation of glutaric acid from cyclopentane, formation of pimelic acid from cycloheptane, and the like.

Figure 1:
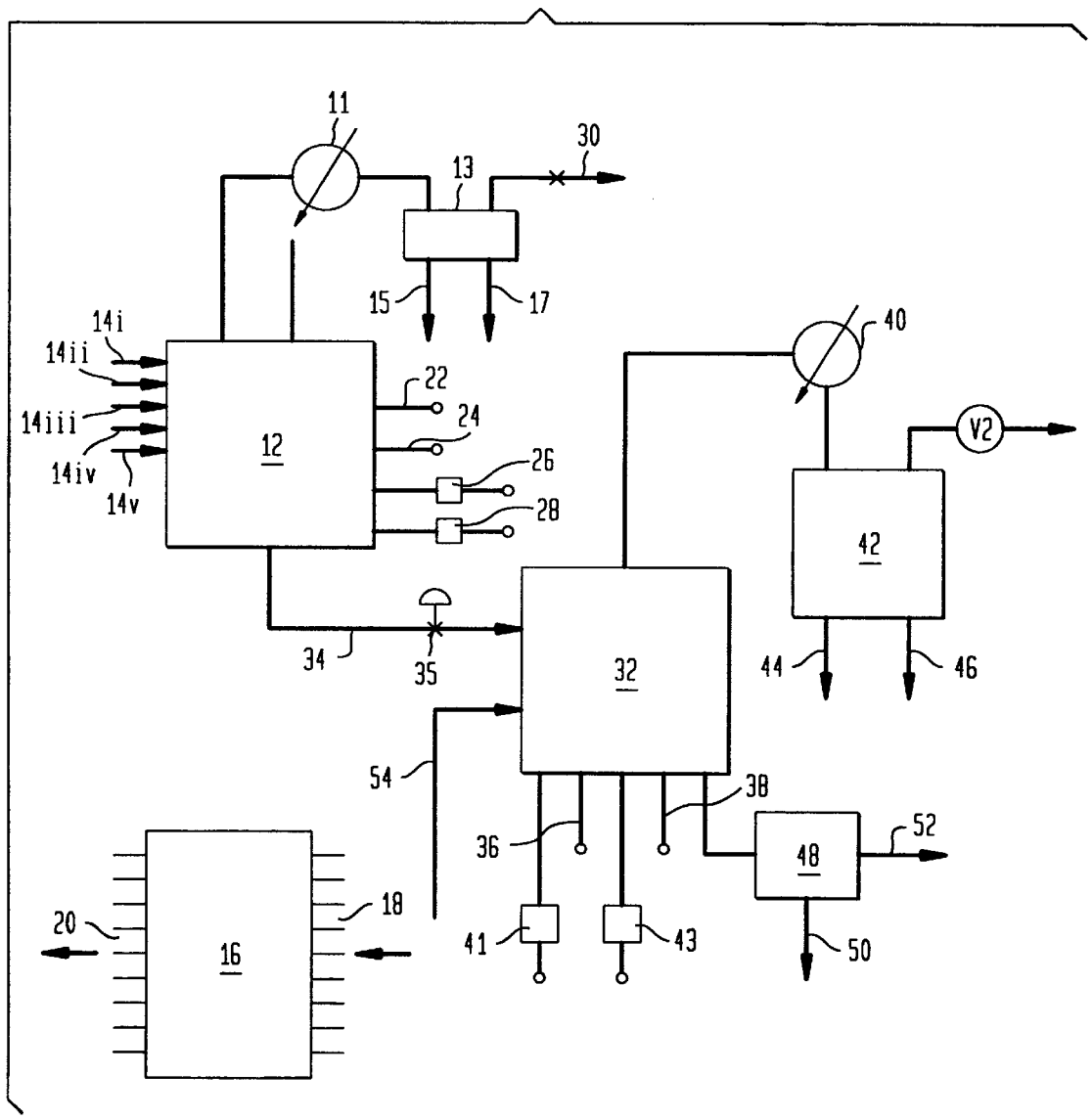
FIG. 1 illustrates a block diagram of a preferred embodiment of the present invention, comprising a first reaction chamber and a second chamber.

Referring now to FIG. 1, there is depicted a device or reactor system 10 according to a preferred embodiment of the instant invention. The device or reactor system 10 comprises a first reaction chamber 12.

The first reaction chamber 12 is connected to a first condenser 40, which in turn is preferably connected to a first retaining chamber 13. The first retaining chamber 13 may also play the role of a decanter, for separating, for example, water of reaction and/or solvent from mainly hydrocarbon through lines 15 and 17, respectively, for example.

Any type of condenser may be used with the miscellaneous chambers of the instant invention, including but not limited to spray condensers, shell and tube heat exchangers, etc.

A number of controlled feeding lines or feeding means are connected to the first reaction chamber 12. These controlled feeding lines or means are a first hydrocarbon feeding line 14i, a first gaseous oxidant feeding line 14ii, a first solvent feeding line 14iii, a first catalyst feeding line 14iv, and a first initiator feeding line 14v. Feeding the respective materials through these controlled feeding lines or feeding means, is controlled by a controller 16, having inputs 18 and outputs 20. Flow rate information from each feeding line is provided to the controller 16 by flowmeters (not shown for purposes of clarity) connected to inputs 18 by well known to the art techniques. Valves or pumps or a combination of both (not shown for purposes of clarity) are connected to respective outputs 20, through which the controller 16 controls the feed rates of the different streams after processing the flow rates information as well as additional information, such as temperature, pressure, analytical data, etc., according to a desired program. The aforementioned feeding lines may merge individually or together, in part or totally, to pre-reaction chamber(s) (not shown) or vessels (not shown), or heat exchangers (not shown), all well known to the art, before they enter the first reaction chamber 12. Such arrangements may be also controlled by the controller 16 through output lines 20.

Connected to the first reaction chamber 12, there are also a temperature monitor 22, and a pressure monitor 24, both connected (not shown) in turn to input lines 18 of the controller 16.

The temperature input obtained by the controller 16 is useful for miscellaneous heat exchangers (not shown), such as heaters and/or coolers (including condensers) for example, either directly connected to the first reaction chamber 12, or through line 30, or through any arrangement of the feeding lines 14i to 14v, to be controlled by the controller 16 through outputs 20 and thus adjust the temperature in the first reaction chamber. This combination provides an example of a first temperature control means for controlling the temperature inside the first reaction chamber 12.

The pressure input obtained by the controller 16 is useful for miscellaneous valves, and/or pumps, etc. (not shown), to be controlled by the controller 16 through outputs 20 and thus adjust the pressure in the first reaction chamber according to a predetermined manner. This combination provides an example of a first pressure control means for controlling the pressure inside the first reaction chamber 12.

Preferably, a chemical analyzer 26 is-also connected to the first reaction chamber 12 for receiving samples of the contents of said first reaction chamber 12, analyzing them, and providing the analysis information to the controller 16, again through input lines 18. The chemical analyzer 26 preferably comprises GC and HPLC instrumentation, and more preferably GC/MS, GC/FID, HPLC/UV and HPLC/MS, for obtaining fast and accurate chemical balance to be provided to the controller 16 for being used for further processing, and finally to be used for the control of the miscellaneous parameters and conditions involved in the operation of the first reaction chamber 12.

Also preferably, a phase analyzer 28, as described in our co-pending U.S. patent application Ser. No. 08/812,847 (of Mark W. Dassel, Eustathios Vassiliou, David C. DeCoster, Ader M. Rostami, and Sharon M. Aldrich, titled "Methods and Devices for Controlling the Reaction Rate of a Hydrocarbon to an Acid by Making Phase-related Adjustments", filed on Mar. 6, 1997, and which is incorporated herein by reference) is connected to the first reaction chamber 12 for receiving samples of the contents of said first reaction chamber 12, phase-analyzing them, and providing the analysis information to the controller 16, again through input lines 18. The results are then provided to the controller 16 for being used for further processing, and finally to be used for the control of the liquid phase conditions inside the first reaction chamber 12.

An off-gas outlet 30 is further connected to the first reaction chamber 12 for removing off-gases by well known to the art techniques.

The first reaction chamber 12 communicates with a second chamber 32 through a first transfer line 34, which first transfer line 34 comprises a valve 35. Preferably, connected to the second vessel 32, there are a second temperature monitor 36, a second pressure monitor 38, a second chemical analyzer 41, and a second phase analyzer 43. In a similar manner as in the case of monitoring the different parameters of the first reaction chamber 12, the second temperature monitor 36, the second pressure monitor 38, the second chemical analyzer 41, and the second phase analyzer 43 are connected to inputs 18 to provide information and enable the controller 16 to control respective parameters and conditions of the contents of the second chamber 32. Thus, they provide means for controlling the second temperature and the second pressure in the second chamber 32, while maintaining a single liquid phase.

Although for continuous reactor systems the first reaction chamber 12 and the second chamber 32 should be individual units, in the case of batch reactors they may be combined in one and the same unit, preferably utilizing only one set of monitors and analyzers.

The second chamber 32 is also connected to a second condenser 40, which in turn is preferably connected to a second retaining chamber 42. The second retaining chamber 42 may also play the role of a decanter, for separating, for example, water of reaction and/or solvent from mainly hydrocarbon through lines 44 and 46, respectively, for example. A vacuum generator V2 may preferably be also connected to the second retaining chamber 42.

The second chamber 32 is preferably further connected to separating means, such as a solids separator 48, for example, for separating at least partially the dibasic acid. Such solids separators may be for example pressure-filtering devices, centrifugal devices, etc. The solids may be transferred out of the solids separator 48 through a solids line 50, and the liquids may be transferred out of the solids separator 48 through a liquids line 52.

A second hydrocarbon feeding line 54 is preferably provided with a flowmeter which gives flow information to input 18 of the controller 16, and it is connected to the second chamber 32. It preferably originates from a hydrocarbon supply vessel (not shown) through pumps and/or valves (not shown), which are connected to output lines 20 and are controlled by the controller 16. The hydrocarbon, such as cyclohexane for example, may be provided to line 54 from line 46, or any other appropriate line or source.

In operation of this embodiment, hydrocarbon, such as cyclohexane for example enters the first reaction chamber 12 through the hydrocarbon feeding line 14*i*. Gaseous oxidant, such as oxygen or a mixture of oxygen with an inert gas for example enters the reaction chamber 12 through the gaseous oxidant feeding line 14*ii*. Solvent, such as acetic acid for example, enters the first reaction chamber 12 through the solvent feeding line 14*iii*. Catalyst, such as a cobalt compound for example, enters the first reaction chamber 12 through the catalyst feeding line 14*iv*. Initiator, such as acetaldehyde or cyclohexanone for example, enters the first reaction chamber 12 through the initiator feeding line 14*v*. As aforementioned, the feeding of the above raw materials does not have to take place directly to the reaction chamber 12. Some or all of the raw materials may be premixed, pre-heated, pre-cooled, or other wise treated before entering the reaction chamber 12, by techniques well known to the art, or as described in our aforementioned patents and patent application. Mixtures of recycled products and/or by-products may also be introduced to the reaction chamber 12, individually or combined with one or more of the fresh raw materials. If the recycling process provides adequate amounts of any of the raw materials, then no additional feed is necessary. The first temperature and the first pressure are arranged by the controller to be such that a reaction of hydrocarbon, cyclohexane for example, and oxidant, oxygen for example, takes place in a controlled manner. Preferable partial first pressures of oxidant are in the range of 50 to 500 psig, and first temperatures in the range of 60° C. to 160° C. These preferable ranges, however, depend on the nature of hydrocarbon and oxidant. In the case that the hydrocarbon is cyclohexane and the oxidant is oxygen, the preferable range of first temperatures is 80° C. to 120° C.

It is highly preferable that the contents of the reaction chamber 12 comprise just a single liquid phase. Examples of how this may be achieved are given in detail in our aforementioned co-pending application T-603. The chemical analyzer 26 and/or the phase analyzer 28 give information to the controller 16, which is utilized to ensure the single liquid phase condition, if so desired. Although it is preferable not to have suspended solids at this stage, the existence of a solid phase suspended within the single or even double liquid phase is not excluded.

Preferably, part of the contents of the first reaction chamber 12 is being transferred to the second chamber 32 through first transfer line 34, where it is being cooled to a second temperature, lower than the first temperature of the first reaction chamber 12. At the second temperature, preferably precipitation of product of oxidation, such as adipic acid for example, occurs. The second temperature is preferably ambient (20° C. to 25° C.) or lower, but not lower than the freezing point of the liquid contents of the second chamber 32. The second temperature is monitored by the second temperature monitor 36, and the temperature information is provided to the controller 16 for further processing.

In some occasions, such as in the case of atomization reaction chambers for example, it is also preferable that another part of the contents of the reaction chamber 12 are recirculated (not shown) from line 34 back to the first reaction chamber 12, preferably through atomization nozzles.

According to the present invention, it is also necessary that despite the fact that the second temperature is lower, and preferably considerably lower, than the first temperature, no second liquid phase is allowed to be formed. By not allowing a second phase to be formed, an undesirable decanting step, especially in the presence of a solid precipitated phase, and its consequences are completely eliminated.

The second temperature may be controlled in a number of different ways. A highly preferable way is by controllably reducing the pressure in the second chamber 32 to attain a value preferably considerably lower than the value of the first pressure prevailing in the first reaction chamber 12. By doing this, two very desirable phenomena take place. First, the temperature is being lowered by evaporation of volatiles, such as cyclohexane or other hydrocarbon for example, due to the reduction of pressure. Second, evaporation of hydrocarbon results in lowering the content of hydrocarbon in the mixture, which favors a single liquid phase. The lowering of hydrocarbon content has to be high enough for maintaining the single liquid phase at the second temperature. If the initial content of the first reaction chamber 12 is low enough, and/or if the conversion of hydrocarbon to dibasic acid is high enough, then there is no need for large amounts of hydrocarbon to be removed from the contents of the second chamber 32 in order to maintain a single liquid phase. In such a case, even additional cold hydrocarbon or other cold matter may be added to the second chamber 32 through the second hydrocarbon feeding line 54 without formation of a second liquid phase. Such matter may preferably be solvent or hydrocarbon.

The hydrocarbon evaporated from the second chamber 32 along with solvent, water, and other gases and/or vaporized liquids is condensed in the second condenser 40, and collected in the second retaining chamber 42, where the water with solvent may be separated from the hydrocarbon with solvent and, either one or both, recirculated (for example to the first reaction chamber 12 or to the second chamber 32) or otherwise treated through lines 44 and 46.

Additional cooling may be provided, if necessary, to the contents of the second chamber 32, by well known to the art techniques, so that at least part, and preferably the majority of the dibasic acid, adipic acid for example, precipitates. In turn, the dibasic acid is separated in solids separator 48, by filtration for example, or any other method well known to the art. The solids are transferred out of the solids separator 48 through solids line 50, and the liquids are transferred out of the of the solids separator 48 through liquids line 52 for further treatment and/or recycling.

The temperature of the second chamber 32 may also be managed by adjusting the composition of the contents of said second chamber 32. For example, heat may be added with simultaneous adjustment of hydrocarbon, such as cyclohexane for example, content. Removal of water with cyclohexane favors the formation and maintenance of a single liquid phase. For example, recycling of cyclohexane from the second retaining chamber 42 to the second chamber 32 through line 46, and simultaneous addition of heat to said second chamber 32, by means of a heating coil (not shown) for example, may lower the content of water and/or cyclohexane in the second chamber 32, and thereby promote the formation and maintenance of a single liquid phase. Further, addition of solvent, also favors the formation and maintenance of a single phase.

The second pressure inside the second chamber 32 is preferably maintained as atmospheric or sub-atmospheric through vacuum generator V2. In some occasions further cooling may be achieved in the second chamber 32 by addition of hydrocarbon or other matter having lower temperature than the temperature of the contents of the second chamber 32, through line 54, as also mentioned earlier.

As aforementioned, in a similar manner as in the case of monitoring the different parameters of the first reaction chamber 12, the second temperature monitor 36, the second pressure monitor 38, the second chemical analyzer 41, the second phase analyzer 43, and flowmeters in lines 34 and 54 are connected to inputs 18 to provide information and enable the controller 16 to control respective parameters and conditions of the contents of the second chamber 32. Thus, they provide means for controlling the temperature and the pressure in the second chamber 32, while maintaining a single liquid phase.

Figure 2:
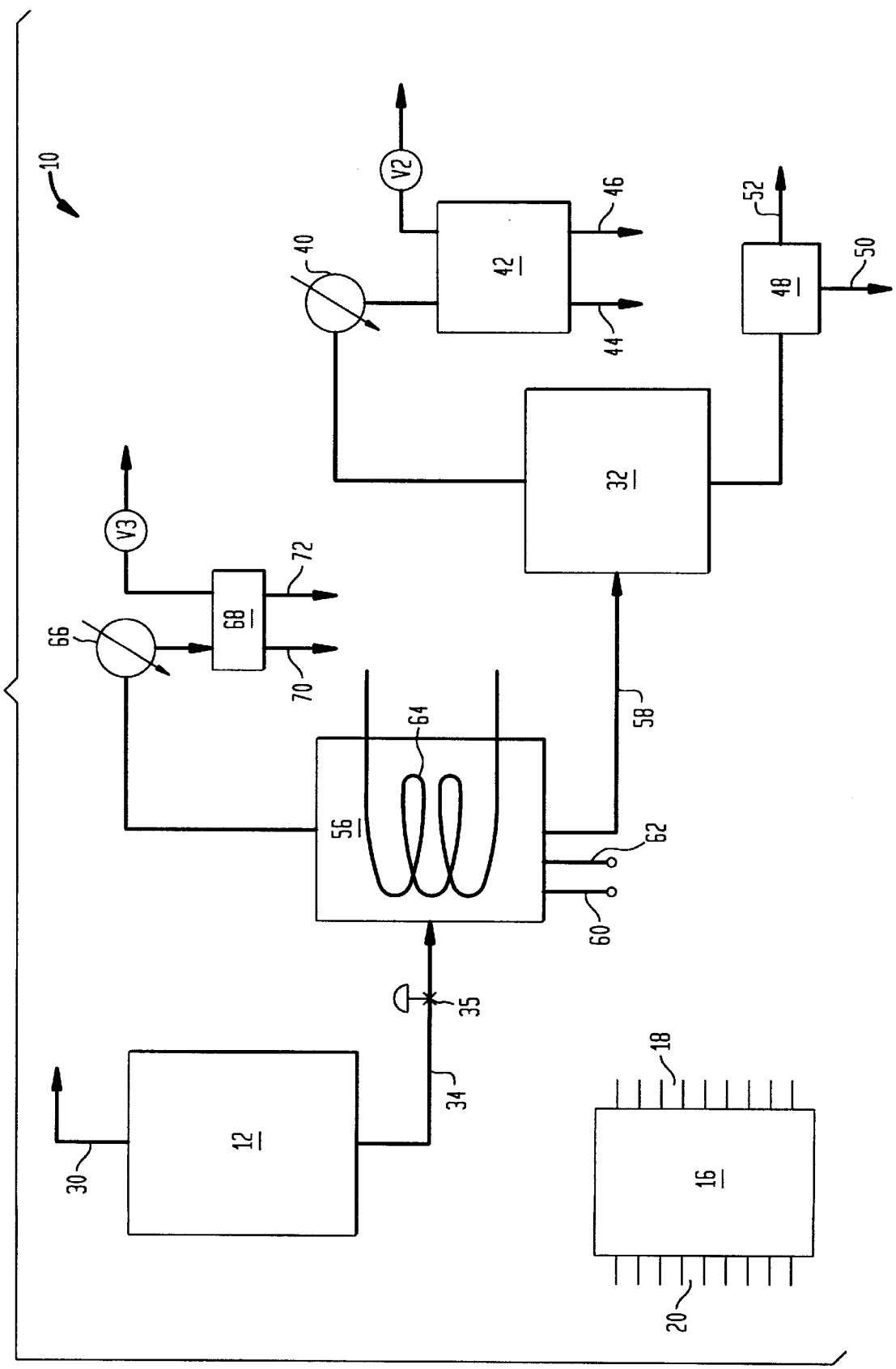
FIG. 2 illustrates a block diagram of another preferred embodiment of the present invention, wherein external heating means have been provided between the first reaction chamber and the second chamber.

In a different preferred embodiment of the present invention, better illustrated in FIG. 2, the device or reactor system 10, comprises, in addition to the other chambers and their accessory elements, a first intermediate chamber 56, which communicates with the first reaction chamber 12 through the first transfer line 34, and with the second chamber 32 through a second transfer line 58.

To the first intermediate chamber 56, there is also connected a first intermediate temperature monitor 60, which monitor is also connected to inputs 18 of the controller 16 for providing temperature information to said controller, which controller in turn controls the temperature inside the chamber 56. This arrangement constitutes first intermediate temperature control means for controlling the temperature in said first intermediate chamber 56.

To the first intermediate chamber 56, there is also connected first intermediate pressure monitor 62, which monitor is also connected to inputs 18 of the controller 16 for providing pressure information to said controller, which controller in turn controls the pressure inside the chamber 56. This arrangement constitutes first intermediate pressure control means for controlling the temperature in said first intermediate chamber 56.

The intermediate chamber 56, further comprises first intermediate external heating means 64, such as a heating coil for example, for providing thermal energy to matter inside the first intermediate chamber 56. The intermediate chamber 56 is also connected to an intermediate condenser 66, which in turn is preferably connected to an intermediate retaining chamber 68. As in the case of the retainer 42, the retainer 68 may also serve as a simple decanter for separating reaction water and /or solvent through line 70, and mainly hydrocarbon through line 72. An intermediate vacuum generator V3 may also be connected to the intermediate retaining chamber 68.

Decanting liquids in absence of a solid phases is substantially less complicated than decanting in the presence of said solid phases.

The operation of this embodiment is similar to the operation of the previous embodiment with the exception that the first pressure prevailing in the first reaction chamber 12 is controllably dropped to a desired first intermediate pressure in the intermediate chamber 56, forcing hydrocarbon and smaller amounts of other volatile materials, such as for example reaction water and/or solvent, to evaporate and be condensed by intermediate condenser 66, thus lowering the content of hydrocarbon in the first intermediate chamber 56, and also removing heat from the system, resulting in lowering the first temperature to a first intermediate temperature. In a continuous operation, which is the preferred type of operation, a stream of liquid from the first reaction chamber 12 is being transferred to the first intermediate chamber 56 through the first transfer line 34.

The first intermediate external heating means 64, provides a controlled and desired amount of heat to the contents of the first intermediate chamber 56, so that further hydrocarbon evaporates. The temperature and the hydrocarbon content of the first intermediate chamber 56 are maintained at such levels so that preferably no substantial precipitation of a solid phase comprising dibasic acid occurs. Higher temperatures and lower contents of hydrocarbon favor the prevention of precipitation, as well as the prevailing of a single liquid phase.

A stream of liquid is also being transferred through the second chamber 32 through the second transfer line 58. The rest of the operation is substantially the same as described in the previous embodiment, with the controller programmed to ensure that at the second temperature prevailing in the second chamber 32 and the amount of hydrocarbon are such that there is only a single liquid phase containing the precipitated dibasic acid, adipic acid for example.

Figure 3:
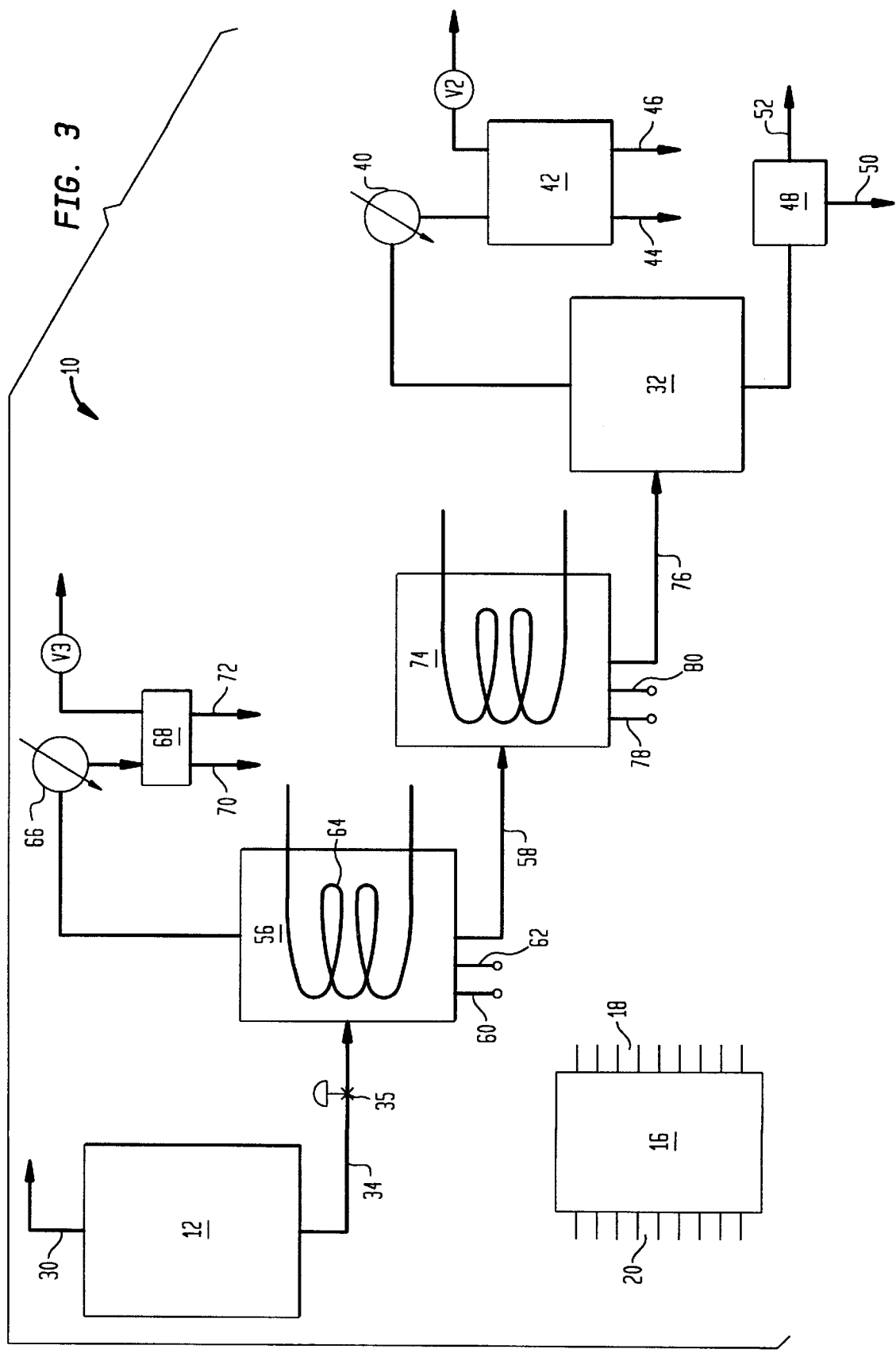
FIG. 3 illustrates a block diagram of still another preferred embodiment of the present invention, wherein both external heating means and external cooling means have been provided between the first reaction chamber and the second chamber.

In a still a different preferred embodiment of the present invention, better illustrated in FIG. 3, the device or reactor system 10, comprises, in addition to the other chambers and their accessory elements, a second intermediate chamber 74, which communicates with the first intermediate chamber 56 through the second transfer line 58, and with the second chamber 32 through a third transfer line 76. Although, for purposes of simplicity, condensers, retaining chambers, vacuum generators, etc., are not shown in all chambers, it should be understood that such elements may be connected to any one of the chambers. In addition, one or more of the vacuum generators may be replaced by let-down valves, open lines, etc.

To the second intermediate chamber 74, there is also connected a second intermediate temperature monitor 78, which monitor is also connected to inputs 18 of the controller 16 for providing temperature information to said controller, which controller in turn controls the temperature inside the chamber 74. This arrangement constitutes second intermediate temperature control means for controlling the temperature in said second intermediate chamber 74.

To the second intermediate chamber 74, there is also connected second intermediate pressure monitor 80, which monitor is also connected to inputs 18 of the controller 16 for providing pressure information to said controller, which controller in turn controls the pressure inside the chamber 74. This arrangement constitutes second intermediate pressure control means for controlling the temperature in said second intermediate chamber 74.

The second intermediate chamber 74, further comprises second intermediate external cooling means 82, such as a cooling coil for example, for removing thermal energy from matter inside the second intermediate chamber 74.

The operation of this embodiment is similar to the operation of the previous embodiments with the exception that the first intermediate temperature prevailing in the first intermediate chamber 56 is reduced in the second intermediate chamber to a second intermediate temperature with substantially no solids precipitation. After addition of heat and removal of an adequate amount of hydrocarbon in the first intermediate chamber 56, heat is removed in the second intermediate chamber 74, so that when the second intermediate pressure, which is preferably the same as the first intermediate pressure, is reduced in the second chamber 32 to the second pressure, the temperature drops adequately for a substantial precipitation of the dibasic acid, adipic acid for example, to occur. Of course, an adequate amount of hydrocarbon, cyclohexane for example, is removed in the first intermediate chamber 56 and the second chamber 32, so that no second liquid phase is formed in the second chamber 32. It is highly preferable to avoid having cooling elements, such as cooling coils for example, in the chamber (in this case second chamber 32) in which the precipitation of the solid phase takes place, since deposits on the coils and plugging problems become a serious problem.

Chemical and/or phase analysis may be conducted on the contents of any of the transfer lines or any of the chambers in any of the embodiments.

It should be understood that according to the present invention, any liquids or gases or off-gases may be recycled totally or partially from any chamber to any other chamber.

A preferable type of controller is a computerized controller, and more preferably a "learning computer" or a "neuro-computer", the functionality of which is known to the art, and which collects information from different places of the device (for example pressure, temperature, chemical or other analysis, etc.), stores this information along with the result (reaction rate, for example), and it is programmed to use this information in the future, along with other data if applicable, to make decisions regarding the action to be taken at each instance.

Although the miscellaneous functions are preferably controlled by a computerized controller, it is possible, according to this invention, to utilize any other type of controller or even manual controls for controlling one or more functions.

Oxidations according to this invention, are nondestructive oxidations, wherein the oxidation product is different than carbon monoxide, carbon dioxide, and a mixture thereof. Of course, small amounts of these compounds may be formed along with the oxidation product, which may be one product or a mixture of products.

Examples include, but of course, are not limited to preparation of $C_5$–$C_8$ aliphatic dibasic acids from the corresponding saturated cycloaliphatic hydrocarbons, such as for example preparation of adipic acid from cyclohexane.

Regarding adipic acid, the preparation of which is especially suited to the methods and apparatuses of this invention, general information may be found in a plethora of U.S. patents, among other references. These, include, but are not limited to:

U.S. Pat. Nos. 2,223,493; 2,589,648; 2,285,914; 3,231,608; 3,234,271; 3,361,806; 3,390,174; 3,530,185; 3,649,685; 3,657,334; 3,957,876; 3,987,100; 4,032,569; 4,105,856; 4,158,739 (glutaric acid); 4,263,453; 4,331,608; 4,606,863; 4,902,827; 5,221,800; and 5,321,157.

Diacids (for example adipic acid, and the like) or other suitable compounds may be reacted, according to well known to the art techniques, with a third reactant selected from a group consisting of a polyol, a polyamine, and a polyamide in a manner to form a polymer of a polyester, or a polyamide, or a (polyimide and/or polyamideimide), respectively. Preferably the polyol, the polyamine, and the polyamide are mainly a diol, a diamine, and a diamide, respectively, in order to avoid excessive cross-linking. The polymer resulting from this reaction may be spun by well known to the art techniques to form fibers.

Examples demonstrating the operation of the instant invention have been given for illustration purposes only, and should not be construed as limiting the scope of this invention in any way. In addition it should be stressed that the preferred embodiments discussed in detail hereinabove, as well as any other embodiments encompassed within the limits of the instant invention, may be practiced individually, or in any combination thereof, according to common sense and/or expert opinion. Individual sections of the embodiments may also be practiced individually or in combination with other individual sections of embodiments or embodiments in their totality, according to the present invention. These combinations also lie within the realm of the present invention. Furthermore, any attempted explanations in the discussion are only speculative and are not intended to narrow the limits of this invention.

All explanations given hereinabove are to be considered as speculative and should not be construed as limiting the breadth of the claims.

What is claimed is:

1. A method of preparing a polymer from a dibasic acid, wherein the dibasic acid is prepared in a reaction zone from a hydrocarbon in a mixture with a solvent, a catalyst and water at a first temperature and at a first pressure, the hydrocarbon being at a hydrocarbon content, the solvent being at a solvent content, and the water being at a water content, the method comprising the steps of:

(a) reacting at least part of the hydrocarbon in the mixture being at the first temperature and at the first pressure with a gaseous oxidant to form at least part of the dibasic acid at a conversion range, lower than substantially complete conversion;

(b) lowering the first temperature to a second temperature with simultaneous at least partial precipitation of the dibasic acid, and with simultaneous removal of an effective amount of hydrocarbon to maintain a single liquid phase at the second temperature;

(c) removing at least part of the precipitated dibasic acid; and (d) reacting the dibasic acid with a reactant selected from a group consisting of a polyol, a polyamine, and a polyamide in a manner to form the polymer of a polyester, or a polyamide, or a polyimide, or polyamideimide.

2. A method as defined in claim 1, further comprising a step of spinning the polymer into fibers.

3. A method as defined in claim 1, wherein the lowering of the first temperature to the second temperature comprises an operation selected from a group consisting of (a) at least partially by evaporating at least part of the hydrocarbon (b) at least partially by lowering the first pressure to a second pressure (c) partially by adding matter having a temperature lower than the first temperature (d) partially by removing heat by external means (e) partially by removing a first amount of heat, and adding a second amount of heat by external means, the first amount of heat being greater than the second amount of heat, and (f) a combination thereof.

4. A method as defined in claim 2, wherein the lowering of the first temperature to the second temperature comprises an operation selected from a group consisting of (a) at least partially by evaporating at least part of the hydrocarbon (b) at least partially by lowering the first pressure to a second pressure (c) partially by adding matter having a temperature lower than the first temperature (d) partially by removing heat by external means (e) partially by removing a first amount of heat, and adding a second amount of heat by external means, the first amount of heat being greater than the second amount of heat, and (f) a combination thereof.

5. A method as defined in claim 1, wherein the maintaining of a single liquid phase is controlled by adjusting the content of hydrocarbon, or water, or solvent, or a combination thereof, at the second temperature.

6. A method as defined in claim 2, wherein the maintaining of a single liquid phase is controlled by adjusting the content of hydrocarbon, or water, or solvent, or a combination thereof, at the second temperature.

7. A method as defined in claim 3, wherein the maintaining of a single liquid phase is controlled by adjusting the content of hydrocarbon, or water, or solvent, or a combination thereof, at the second temperature.

8. A method as defined in claim 4, wherein the maintaining of a single liquid phase is controlled by adjusting the content of hydrocarbon, or water, or solvent, or a combination thereof, at the second temperature.

9. A method as defined in claim 1, wherein the hydrocarbon comprises cyclohexane, the gaseous oxidant comprises oxygen, the dibasic acid comprises adipic acid, the solvent comprises acetic acid, and the catalyst comprises a multivalent heavy metal ion.

10. A method as defined in claim 2, wherein the hydrocarbon comprises cyclohexane, the gaseous oxidant comprises oxygen, the dibasic acid comprises adipic acid, the solvent comprises acetic acid, and the catalyst comprises a multivalent heavy metal ion.

11. A method as defined in claim 3, wherein the hydrocarbon comprises cyclohexane, the gaseous oxidant comprises oxygen, the dibasic acid comprises adipic acid, the solvent comprises acetic acid, and the catalyst comprises a multivalent heavy metal ion.

12. A method as defined in claim 4, wherein the hydrocarbon comprises cyclohexane, the gaseous oxidant comprises oxygen, the dibasic acid comprises adipic acid, the solvent comprises acetic acid, and the catalyst comprises a multivalent heavy metal ion.

13. A method as defined in claim 5, wherein the hydrocarbon comprises cyclohexane, the gaseous oxidant comprises oxygen, the dibasic acid comprises adipic acid, the solvent comprises acetic acid, and the catalyst comprises a multivalent heavy metal ion.

14. A method as defined in claim 6, wherein the hydrocarbon comprises cyclohexane, the gaseous oxidant comprises oxygen, the dibasic acid comprises adipic acid, the solvent comprises acetic acid, and the catalyst comprises a multivalent heavy metal ion.

15. A method as defined in claim 7, wherein the hydrocarbon comprises cyclohexane, the gaseous oxidant comprises oxygen, the dibasic acid comprises adipic acid, the solvent comprises acetic acid, and the catalyst comprises a multivalent heavy metal ion.

16. A method as defined in claim 8, wherein the hydrocarbon comprises cyclohexane, the gaseous oxidant comprises oxygen, the dibasic acid comprises adipic acid, the solvent comprises acetic acid, and the catalyst comprises a multivalent heavy metal ion.

17. A method of preparing a polymer from a dibasic acid, wherein the dibasic acid is prepared in a reaction zone from a hydrocarbon in a mixture with a solvent, a catalyst and water at a first temperature and at a first pressure, the hydrocarbon being at a hydrocarbon content, the solvent being at a solvent content, and the water being at a water content, the method comprising the steps of:

(a) reacting at least part of the hydrocarbon in the mixture being at the first temperature and at the first pressure with a gaseous oxidant to form at least part of the dibasic acid at a conversion range, lower than substantially complete conversion;

(b) lowering the first temperature to a second temperature, while maintaining a single liquid phase at the second temperature, wherein the lowering of the first temperature to the second temperature involves an intermediate step of lowering the first temperature to a first intermediate temperature by lowering the first pressure to an intermediate pressure to form a first intermediate liquid phase containing no substantial amount of solid phase, and wherein lowering of the intermediate temperature to the second temperature is conducted with simultaneous at least partial precipitation of the dibasic acid, and with simultaneous removal of an effective amount of hydrocarbon to maintain a single liquid phase at the second temperature;

(c) removing at least part of the precipitated dibasic acid; and (d) reacting the dibasic acid with a reactant selected from a group consisting of a polyol, a polyamine, and a polyamide in a manner to form the polymer of a polyester, or a polyamide, or a polyimide, or polyamideimide.

18. A method as defined in claim 17, further comprising a step of spinning the polymer into fibers.

19. A method as defined in claim 17, wherein the lowering of the first temperature to the second temperature comprises an operation selected from a group consisting of (a) at least partially by evaporating at least part of the hydrocarbon (b) at least partially by lowering the first pressure to a second pressure (c) partially by adding matter having a temperature lower than the first temperature (d) partially by removing heat by external means (e) partially by removing a first amount of heat, and adding a second amount of heat by external means, the first amount of heat being greater than the second amount of heat, and (f) a combination thereof.

20. A method as defined in claim 18, wherein the lowering of the first temperature to the second temperature comprises an operation selected from a group consisting of (a) at least partially by evaporating at least part of the hydrocarbon (b) at least partially by lowering the first pressure to a second pressure (c) partially by adding matter having a temperature lower than the first temperature (d) partially by removing heat by external means; (e) partially by removing a first amount of heat, and adding a second amount of heat by external means, the first amount of heat being greater than the second amount of heat, and (f) a combination thereof.

21. A method as defined in claim 17, wherein the maintaining of a single liquid phase is controlled by adjusting the content of hydrocarbon, or water, or solvent, or a combination thereof, at the second temperature.

22. A method as defined in claim 18, wherein the maintaining of a single liquid phase is controlled by adjusting the content of hydrocarbon, or water, or solvent, or a combination thereof, at the second temperature.

23. A method as defined in claim 19, wherein the maintaining of a single liquid phase is controlled by adjusting the content of hydrocarbon, or water, or solvent, or a combination thereof, at the second temperature.

24. A method as defined in claim 20, wherein the maintaining of a single liquid phase is controlled by adjusting the content of hydrocarbon, or water, or solvent, or a combination thereof, at the second temperature.

25. A method as defined in claim 17, wherein the hydrocarbon comprises cyclohexane, the gaseous oxidant comprises oxygen, the dibasic acid comprises adipic acid, the solvent comprises acetic acid, and the catalyst comprises a multivalent heavy metal ion.

26. A method as defined in claim 18, wherein the hydrocarbon comprises cyclohexane, the gaseous oxidant comprises oxygen, the dibasic acid comprises adipic acid, the solvent comprises acetic acid, and the catalyst comprises a multivalent heavy metal ion.

27. A method as defined in claim 19, wherein the hydrocarbon comprises cyclohexane, the gaseous oxidant comprises oxygen, the dibasic acid comprises adipic acid, the solvent comprises acetic acid, and the catalyst comprises a multivalent heavy metal ion.

28. A method as defined in claim 20, wherein the hydrocarbon comprises cyclohexane, the gaseous oxidant comprises oxygen, the dibasic acid comprises adipic acid, the solvent comprises acetic acid, and the catalyst comprises a multivalent heavy metal ion.

29. A method as defined in claim 21, wherein the hydrocarbon comprises cyclohexane, the gaseous oxidant comprises oxygen, the dibasic acid comprises adipic acid, the solvent comprises acetic acid, and the catalyst comprises a multivalent heavy metal ion.

30. A method as defined in claim 22, wherein the hydrocarbon comprises cyclohexane, the gaseous oxidant comprises oxygen, the dibasic acid comprises adipic acid, the solvent comprises acetic acid, and the catalyst comprises a multivalent heavy metal ion.

31. A method as defined in claim 23, wherein the hydrocarbon comprises cyclohexane, the gaseous oxidant comprises oxygen, the dibasic acid comprises adipic acid, the solvent comprises acetic acid, and the catalyst comprises a multivalent heavy metal ion.

32. A method as defined in claim 26, wherein the hydrocarbon comprises cyclohexane, the gaseous oxidant comprises oxygen, the dibasic acid comprises adipic acid, the solvent comprises acetic acid, and the catalyst comprises a multivalent heavy metal ion.

* * * * *